(12) United States Patent (10) Patent No.: US 8,268,619 B2
Giacomello et al. (45) Date of Patent: Sep. 18, 2012

(54) METHOD FOR THE ISOLATION AND EXPANSION OF CARDIAC STEM CELLS FROM BIOPSY

(75) Inventors: Alessandro Giacomello, Rome (IT); Elisa Messina, Rome (IT); Massimo Battaglia, Rome (IT); Giacomo Frati, Rome (IT)

(73) Assignee: Universita Degli Studi di Roma "La Sapienza", Rome (IT)

( * ) Notice: Subject to any disclaimer, the term of this patent is extended or adjusted under 35 U.S.C. 154(b) by 524 days.

(21) Appl. No.: 10/567,008

(22) PCT Filed: Jul. 29, 2004

(86) PCT No.: PCT/IT2004/000421
§ 371 (c)(1),
(2), (4) Date: Jul. 13, 2006

(87) PCT Pub. No.: WO2005/012510
PCT Pub. Date: Feb. 10, 2005

(65) Prior Publication Data
US 2007/0020758 A1    Jan. 25, 2007

(30) Foreign Application Priority Data
Jul. 31, 2003    (IT) .............................. RM2003A0376

(51) Int. Cl.
C12N 5/00        (2006.01)
C12N 5/02        (2006.01)
(52) U.S. Cl. ........................................ 435/377; 435/383
(58) Field of Classification Search .................. 435/377, 435/383
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,921,482 A | 5/1990 | Hammerslag et al. |
| 4,960,134 A | 10/1990 | Webster, Jr. |
| 5,052,402 A | 10/1991 | Bencini et al. |
| 5,175,004 A | 12/1992 | Matsumura |
| 5,199,950 A | 4/1993 | Schmitt |
| 5,287,857 A | 2/1994 | Mann |
| 5,383,852 A | 1/1995 | Stevens-Wright |
| 5,436,128 A | 7/1995 | Harpold et al. |
| 5,492,825 A | 2/1996 | Jan et al. |
| 5,616,568 A | 4/1997 | Prestwich et al. |
| 5,670,335 A | 9/1997 | Jan et al. |
| 5,702,433 A | 12/1997 | Taylor et al. |
| 5,782,748 A | 7/1998 | Palmer et al. |
| 5,856,155 A | 1/1999 | Li |
| 5,874,417 A | 2/1999 | Prestwich et al. |
| 5,955,275 A | 9/1999 | Kamb |
| 5,957,863 A | 9/1999 | Koblish et al. |
| 5,981,165 A | 11/1999 | Weiss et al. |
| 6,074,408 A | 6/2000 | Freeman |
| 6,203,487 B1 | 3/2001 | Consigny |
| 6,224,587 B1 | 5/2001 | Gibson |
| 6,387,369 B1 | 5/2002 | Pittenger et al. |
| 6,572,611 B1 | 6/2003 | Falwell |
| 6,783,510 B1 | 8/2004 | Gibson et al. |
| 6,805,860 B1 | 10/2004 | Alt |
| 7,034,008 B2 | 4/2006 | Donahue et al. |
| 7,037,648 B1 | 5/2006 | Marban |
| 7,138,275 B2 | 11/2006 | Kremer et al. |
| 7,220,582 B2 | 5/2007 | Epstein et al. |
| 7,259,011 B2 | 8/2007 | Lucas et al. |
| 7,452,532 B2 | 11/2008 | Alt |
| 7,470,425 B2 | 12/2008 | Vacanti et al. |
| 7,514,074 B2 | 4/2009 | Pittenger et al. |
| 7,517,686 B2 | 4/2009 | Kremer et al. |
| 7,547,674 B2 | 6/2009 | Anversa et al. |
| 7,837,631 B2 | 11/2010 | Diamond et al. |
| 7,875,451 B2 | 1/2011 | Murry et al. |
| 8,008,254 B2 | 8/2011 | Anversa |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2003/0054973 A1 | 3/2003 | Anversa |
| 2003/0161817 A1 | 8/2003 | Young et al. |
| 2004/0018174 A1 | 1/2004 | Palasis |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0110287 A1 | 6/2004 | Clarke et al. |

(Continued)

FOREIGN PATENT DOCUMENTS

EP    1254952    11/2002
(Continued)

OTHER PUBLICATIONS

Jackson et al., Regeneration of ischemic cardiac muscle and vascular endothelium by adult stem cells. J Clin Invest. 107(11):1395-402, 2001.*
Beltrami et al., Beltrami et al., Adult cardiac stem cells are multipotent and support myocardial regeneration, Cell, 114(6):763-76, 2003.*
Oh et al., Cardiac progenitor cells from adult myocardium: homing, differentiation, and fusion after infarction, Proc Natl Acad Sci U S A. 100(21):12313-8, 2003.*
de Pomerai et al., Influence of serum factors on the prevalence of "normal" and "foreign" differentiation pathways in cultures of chick embryo neuroretinal cells, J Embryol Exp Morphol. 62:291-308, 1981.*
PCT International Search Report, for Universita Degli Studi Di Roma, International Application No. PCT/IT2004/000421, Filed Jul. 29, 2004.

(Continued)

Primary Examiner — Wu-Cheng Winston Shen
(74) Attorney, Agent, or Firm — Knobbe Martens Olson & Bear, LLP

(57) ABSTRACT

Method for the isolation, expansion and preservation of cardiac stem cells from human or animal tissue biopsy samples to be employed in cell transplantation and functional repair of the myocardium or other organs. Cells may also be used in gene therapy for treating genetic cardiomyopathies, for treating ischemic heart diseases and for setting in vitro models to study drugs.

14 Claims, 4 Drawing Sheets

U.S. PATENT DOCUMENTS

| | | | |
|---|---|---|---|
| 2004/0136966 A1 | 7/2004 | Anversa et al. |
| 2004/0137621 A1 | 7/2004 | Rosen et al. |
| 2005/0074880 A1 | 4/2005 | Sang et al. |
| 2005/0176620 A1 | 8/2005 | Prestwich et al. |
| 2005/0255588 A1 | 11/2005 | Young et al. |
| 2005/0260750 A1 | 11/2005 | Kerr-Conte et al. |
| 2006/0025713 A1 | 2/2006 | Rosengart et al. |
| 2006/0083712 A1 | 4/2006 | Anversa |
| 2006/0198829 A1 | 9/2006 | Rosen et al. |
| 2006/0234375 A1 | 10/2006 | Doronin et al. |
| 2006/0239980 A1 | 10/2006 | Bernad Miana et al. |
| 2006/0239983 A1 | 10/2006 | Anversa |
| 2006/0281791 A1 | 12/2006 | Keating et al. |
| 2007/0014869 A1 | 1/2007 | Matheny |
| 2007/0020758 A1 | 1/2007 | Giacomello et al. |
| 2007/0054397 A1 | 3/2007 | Ott et al. |
| 2007/0072291 A1 | 3/2007 | Kremer et al. |
| 2007/0129296 A1 | 6/2007 | Zhou |
| 2007/0248580 A1 | 10/2007 | Garcia Castro et al. |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0267921 A1 | 10/2008 | Marban et al. |
| 2008/0274998 A1 | 11/2008 | Cohen et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0180998 A1 | 7/2009 | Anversa et al. |
| 2009/0317369 A1 | 12/2009 | Hosoda et al. |
| 2011/0091428 A1 | 4/2011 | Anversa |
| 2011/0123500 A1 | 5/2011 | Anversa et al. |
| 2011/0152835 A1 | 6/2011 | Anversa |

FOREIGN PATENT DOCUMENTS

| | | |
|---|---|---|
| WO | WO 99/49015 A2 | 9/1999 |
| WO | WO 01/48151 | 7/2001 |
| WO | WO 02/09650 A2 | 2/2002 |
| WO | WO02/13760 | 2/2002 |
| WO | WO03/006950 | 1/2003 |
| WO | WO03/008535 | 1/2003 |
| WO | WO 03/103611 | 12/2003 |
| WO | WO 2004/044142 | 5/2004 |
| WO | WO2005/012510 | 2/2005 |
| WO | WO2006/052925 | 5/2006 |
| WO | WO 2007/100530 | 9/2007 |
| WO | WO2008/058273 | 5/2008 |
| WO | WO 2009/032456 | 3/2009 |
| WO | WO2009/062143 | 5/2009 |
| WO | WO2009/073518 | 6/2009 |
| WO | WO2009/073594 | 6/2009 |
| WO | WO2009/073616 | 6/2009 |
| WO | WO2009/073618 | 6/2009 |
| WO | WO 2009/149956 | 12/2009 |
| WO | WO2009/152111 | 12/2009 |
| WO | WO 2010/059806 | 5/2010 |
| WO | WO 2010/083466 | 7/2010 |
| WO | WO 2010/118059 | 10/2010 |
| WO | WO 2011/056685 | 5/2011 |
| WO | WO 2011/057249 | 5/2011 |
| WO | WO 2011/057251 | 5/2011 |

OTHER PUBLICATIONS

Beltrami, et al., "Adult cardiac stem cells are multipotent and support myocardial regeneration", Cell, vol. 114, No. 6, pp. 763-776 (2003).

Oh, et al., "Cardiac muscle plasticity in adult and embryo by heart-derived progenitor cells", Annals of The New York Academy of Sciences, vol. 1015, pp. 182-189 (2004).

Anversa, P. et al., Primitive cells and tissue regeneration. Circ. Res. 92:579-92 (2003).

Barile L. et al., Endogenous Cardiac Stem Cells. Prog. Cardiovas. Dis. 50(1):31-48 (2007).

Barile, L. et al., Cardiac stem cells: isolation, expansion and experimental use for myocardial regeneration. Nat. Clin. Pract. Cardiovasc. Med. 4 Suppl 1: S9-S14 (2007).

Barth AS et al., Lentiviral vectors bearing the cardiac promoter of the Na+-Ca2+ exchanger report cardiogenic differentiation in stem cells. Mol. Ther. 16(5):957-964 (2008).

Beltrami, AP et al., Evidence that human cardiac myocytes divide after myocardial infarction. N. Engl. J. Med. 344: 1750-1757 (2001).

Benardeau, A. et al., Primary culture of human atrial myocytes is associated with the appearance of structural and functional characteristics of immature myocardium. J. Mol. Cell Cardiol. 29: 1307-1320 (1997).

Dispersyn, GD et al., Adult rabbit cardiomyocytes undergo hibernation-like dedifferentiation when co-cultured with cardiac fibroblasts. Cardiovasc. Res. 57: 230-240 (2001).

Dispersyn, GD et al., Dissociation of cardiomyocyte apoptosis and dedifferentiation in infarct border zones. Eur. Heart J. 23:849-857 (2002).

Donahue, et al., Ultrarapid, highly efficient viral gene transfer to the heart, Proc. Natl. Acad. Sci. USA 94:4664-4668 (1997).

Driesen, RB et al., Structural adaptation in adult rabbit ventricular myocytes: influence of dynamic physical interaction with fibroblasts. Cell. Biochem. Biophys. 44: 119-128 (2006).

Driesen, RB et al., Structural remodeling of cardiomyocytes in the border zone of infarcted rabbit heart. Mol. Cell. Biochem (2007).

Engle, FB et al. "p38 Map kinase inhibition enables proliferation of adult mammalian cardiomyocytes", Genes & Dev., May 2005, vol. 19, No. 10, pp. 1175-1187.

Kaab, et al., Ionic mechanism of action potential prolongation in ventricular myocytes from dogs with pacing-induced heart failure. Circulation Research, vol. 78, No. 2, 262 (1996).

Lee, et al., Cardiac gene transfer by intracoronary infusion of adenovirus vector-mediated reporter gene in the transplanted mouse heart. J. Thorac, and Cardio. Surg., 111:246 (1996).

Lyngbaek, S et al., Cardiac regeneration by resident stem and progenitor cells in the adult heart. Basic Res. Cardiol. 102: 101-114 (2007).

Marban, E, Big cells, little cells, stem cells: agents of cardiac plasticity. Circ Res. 100(4):445-6 (2007).

McGann, CJ et al., Mammalian myotube dedifferentiation induced by newt regeneration extract. Proc. Natl. Acad. Sci. USA 98, 13699-704 (2001).

Nadal-Ginard et al, Myocyte death, growth, and regeneration in cardiac hypertrophy and failure. Circ. Res. 92(2):139-50 (2003).

Nadal-Ginard et al., A matter of life and death: cardiac myocyte apoptosis and regeneration. J. Clin. Invest. 111: 1457-9 (2003).

Odelberg, SJ, Inducing cellular dedifferentiation: a potential method for enhancing endogenous regeneration in mammals., Semin Cell Dev. Biol., 13(5):335-43 (2002).

Odelberg, SJ et al., Dedifferentiation of mammalian myotubes induced by msx1. Cell 103(7):1099-1109 (2000).

Passier, R et al., Origin and use of embryonic and adult stem cells in differentiation and tissue repair. Cardiovasc. Res. 58(2):324-35 (2003).

Rucker-Martin, C et al., Dedifferentiation of atrial myocytes during atrial fibrillation: role of fibroblast proliferation in vitro. Cardiovasc. Res. 55: 38-52 (2002).

Smith et al., Stem Cells in the heart: what's the buzz all about? Part 1: Preclinical considerations. Heart Rhythm 5(5):749-757(2008).

Smith et al., Stem Cells in the heart: what's the buzz all about? Part 2: Arrhythmic risks and clinical studies. Heart Rhythm 5(6):880-887 (2008).

Smith, RR et al., Regenerative potential of cardiosphere-derived cells expanded from percutaneous endomyocardial biopsy specimens. Circulation 115: 896-908 (2007).

Sussman et al., Myocardial aging and senescence: where have the stem cells gone? Annu Rev. Physiol. 66:29-48 (2004).

Torella, D et al., Cardiac stem cell and myocyte aging, heart failure, and insulin-like growth factor-1 overexpression. Circ. Res 94:514-24 (2004).

Torella, D et al., Resident human cardiac stem cells: role in cardiac cellular homeostasis and potential for myocardial regeneration. Nat. Clin. Pract. Cardiovasc. Med. 3 Suppl 1:S8-13 (2006).

Urbanek, K et al., Cardiac Stem Cells Possess Growth Factor Receptor Systems That After Activation Regenerate the Infarcted Myocardium, Improving Ventricular Function and Long-term Survival. Circ. Res. 97:663-673 (2005).

Urbanek, K et al., Intense myocyte formation from cardiac stem cells in human cardiac hypertrophy. Proc. Natl. Acad. Sci. USA 100(18):10440-5 (2003).

Urbanek, K et al., Myocardial regeneration by activation of multipotent cardiac stem cells in ischemic heart failure. Proc. Natl. Acad. Sci. USA 102(24):8692-7 (2005).

Von Harsdorf, R, Can cardiomyocytes divide? Heart 86: 481-482 (2001).

Walder, S et al., Up-regulation of neural stem cell markers suggests the occurrence of dedifferentiation in regenerating spinal cord. Dev. Genes Evol. 213: 625-630 (2003).

Wu et al., Cellular Therapy and Myocardial tissue engineering: the role of adult stem and progenitor cells. Eur. J. of Cardio-Thoracic Surg. 30:770-781 (2006).

Zammit, PS et. al, The skeletal muscle satellite cell: stem cell or son of stem cell? Differentiation 68: 193-204 (2001).

Duff et al., "CD105 is important for angiogenesis: evidence and potential applications," FASEB J, Jun. 2003, vol. 17(9), pp. 984-992.

D.C. Andersen et al., "Murine 'Cardiospheres' Are Not a Source of Stem Cells with Cardiomyogenic Potential," Stem Cells, 2009, vol. 27, No. 7, pp. 1571-1581.

Christmann et al., Biomaterials for the Treatment of Myocardial Infarction, J. Am. Coll. of Cardiol. (2006) vol. 48(5): 907-913.

Eschenhagen et al., Engineering Myocardial Tissue, Circ Res (2005) vol. 97:1220-1231.

Harvey, "Molecular Determinants of Cardiac Development and Congenital Disease," Mouse Development, Patterning, Morphogenesis, and Organogensis, Chapter 16, pp. 331-370.

Potapova et al., Enhanced recovery of mechanical function in the canine heart by seeding an extracellular matrix patch with mesenchymal stem cells committed to a cardiac lineage, Am. J. Phys. (2008) vol. 295:H2257-H2263.

Ventura et al., Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts, JBC (2007) vol. 282(19):14243-14252.

Messina, Elisa et al.; Isolation and Expansion of Adult Cardiac Stem Cells from Human and Murine Heart; Oct. 29, 2004; pp. 911-921; vol. 95; Circulation Research; Cellular Biology; American Heart Association.

Y. Tomita et al.; Cardiac Neural Crest Cells Contribute to the Dorman Multipotent Stem Cell in the Mammalian Heart, Journal of Cell Biology, Sep. 26, 2005, vol. 170, No. 7, pp. 1135-1148.

Abela et al., A New Method for Isolation of Cardiac Myocytes by Percutaneous Endomycardial Biopsy, Catheterization and Cardiovascular Diagnosis, 1996, 37:227-230.

Ausma et al., "Dedifferentiation of atrial cardiomyocytes: from in vivo to in vitro", Cardiovascular Research, Jul. 2002, vol. 55(1), pp. 9-12.

Balser et al., Global parameter optimization for cardiac potassium channel gating models, Biophys. J., Mar. 1990, vol. 57, pp. 433-444.

Balser et al., Local Anesthetics as Effectors of Allosteric Gating, J. Clin. Invest., Dec. 1996, vol. 98(12), pp. 2874-2886.

Barr et al., Gene Therapy, Jan. 1994, vol. 1(1), pp. 51-58.

Barry et al., Differential Expression of Voltage-Gated K+ Channel Subunits in Adult Rat Heart, Circulation Research, 1995, vol. 77, pp. 361-369.

Bird et al., "The human adult cardiomyocyte phenotype", Cardiovascular Research, May 1, 2003, vol. 58(2), pp. 423-434.

Bosnali et al., "Generation of transducible versions of transcription factors Oct4 and Sox2," Biological Chemistry, Walter De Gruyter GmbH & Co., Berlin, DE, vol. 389(7), Jul. 1, 2008, pp. 851-861.

Chen et al., Vascular endothelial growth factor promotes cardiomyocyte differentiation of embryonic stem cells, Am J Physiol Heart Circ Physiol, Oct. 2006, vol. 291(4), pp. H1653-1658.

Deal et al., Molecular Physiology of Cardiac Potassium Channels, Physiological Reviews, Jan. 1996, vol. 76(1), pp. 49-67.

Dixon et al., Quantitative Analysis of Potassium Channel mRNA Expression in Atrial and Ventricular Muscle of Rats, Circulation Research, 1994, vol. 75, pp. 252-260.

Dixon et al., Role of the Kv4.3 K+ Channel in Ventricular Muscle, Circulation Research, 1996, vol. 79, pp. 659-668.

Engel et al., FGF1/p38 Map kinase inhibitor therapy induces cardiomyocyte mitosis, reduces scarring, and rescues function after myocardial infarction, Proc Nat Acad Sci (USA), Oct. 17, 2006, vol. 103(42), pp. 15546-15551.

Fiset et al., Shal-type channels contribute to the $Ca^{2+}$-independent transient outward $K^+$ current in rat ventricle, J. Physiology, 1997, vol. 500(1), pp. 51-64.

Gidh-Jain et al., Differential Expression of Voltage-Gated K+ Channel Genes in Left Ventricular Remodeled Myocardium After Experimental Myocardial Infarction, Circulation Research, 1996, vol. 79, pp. 669-675.

Glover et al., Reduction of infarct size and postschemic inflammation from ATL-146e, a highly selective adenosine A2A receptor agonist in reperfused canine myocardium, Amer J Physiol Heart Circ Physiol, Apr. 2005, vol. 288(4), pp. H1851-H1858.

Good et al., β-Amyloid Peptide Blocks the Fast-Inactivating K+ Current in Rat Hippocampal Neurons, Biophysical Journal, Jan. 1996, vol. 70, pp. 296-304.

Heng et al., "Incorporating protein transduction domains (PTD) within recombinant 'fusion' transcription factors. A novel strategy for directing stem cell differentiation?" Biomedicine and Pharmacotherapy, Elsevier, Paris, FR, vol. 59(3), Apr. 1, 2005, pp. 132-134.

Kim et al., "Generation of human induced pluripotent stem cells by direct delivery of reprogramming proteins," Cell Stem Cell, Jun. 5, 2009, vol. 4(6), pp. 472-476.

Kuhn et al., Periostin induces proliferation of differentiated cardiomyocytes and promotes cardiac repair, Nature Medicine, Aug. 2007, vol. 13(8), pp. 962-969. Abstract only.

Kwon et al., "Cellular Manipulation of Human Embryonic Stem Cells by TAT-PDX1 Protein Transduction," Molecular Therapy, Academic Press, San Diego, CA, US, vol. 12(1), Jul. 1, 2005, pp. 28-32.

Li et al., Molecular, Cellular, and Functional Phenotypes of Human Cardiac Stem Cells Dependent Upon Monolayer Versus Three-Dimensional Culture Conditions, Circulation Research, Dec. 4, 2009, vol. 105(12).

Li et al., Expansion of human cardiac stem cells in physiological oxygen improves cell production efficiency and potency for myocardial repair, Cardiovascular Research, Aug. 21, 2010.

Li et al., Stem Cell Technology: Epigenetics, Genomics, Proteomics, and Metabonomics, Stem Cells 2010; vol. 28, pp. 1178-1185.

Maletic-Savatic et al., Differential Spatiotemporal Expression of K+ Channel Polypeptides in Rat Hippocampal Neurons Developing in situ and in vitro, Journal of Neuroscience, May 1995, vol. 15(5), pp. 3840-3851.

Marshall et al., The Jellyfish Green Fluorescent Protein: A New Tool for Studying Ion Channel Express and Function, Neuron, 1995, vol. 14, pp. 211-215.

Montessuit et al., "Regulation of glucose transporter expression in cardiac myocytes: p38 MAPK is a strong inducer of GLUT4", Cardiovascular Research, Oxford University Press, Oct. 1, 2004, vol. 64(1), pp. 94-104.

Montessuit et al., "Retinoic acids increase expression of GLUT4 in dedifferentiated and hypertrophied cardiac myocytes", Basic Research in Cardiology, Steinkopff-Verlag, DA, Jan. 1, 2006, vol. 101(1), pp. 27-35.

Plotnikov et al., Biologial Pacemaker Implanted in Canine Left Bundle Branch Provides Ventricular Escape Rhythms that Have Physiologically Acceptable Rates, Circulation, Feb. 3, 2004, vol. 109, pp. 506-512.

Ribera, Homogeneous Development of Electrical Excitability via Heterogeneous Ion Channel Expression, Journal of Neuroscience, Feb. 1, 1996, vol. 16(3), pp. 1123-1130.

Risepro et al., Hand1 regulates cardiomyocyte proliferation versus differentiation in the developing heart, Development, Nov. 2006, vol. 133(22), pp. 4595-4606. Abstract only.

Rudy, Diversity and Ubiquity of K Channels, Neuroscience, 1988, vol. 25(3), pp. 729-749.

Serodio et al., Cloning of a Novel Component of A-Type K+ Channels Operating at Subthreshold Potentials With Unique Expression in Heart and Brain, Journal of Neurophysiology, May 1996, vol. 75(5), pp. 2174-2179.

Srivastava et al., Thymosin beta4 is cardioprotective after myocardial infarction, Ann NY Acad Sci, Sep. 2007, vol. 1112, pp. 161-170. Abstract only.

Takahashi et al., "Induction of pluripotent stem cells from adult human fibroblasts by defined factors," Cell, Cell Press, Cambridge, MA, US, vol. 131(5), Nov. 30, 2007, pp. 861-872.

Wagner, The state of the art in antisense research, Nature Medicine, Nov. 1995, vol. 1(11), pp. 1116-1118.

Yu et al., "Induced pluripotent stem cell lines derived from human somatic cells," Science, American Association for the Advancement of Science, US, vol. 318(5858), Dec. 21, 2007, pp,. 1917-1920.

Zhang et al., "Do cardiac stem cells arise from cardiomyocyte dedifferentiation?", Circulation Research, Nov. 2006, vol. 99(11), p. 1278. Abstract only.

Zhou et al., "Generation of Induced Pluripotent Stem Cells Using Recombinant Proteins," Cell Stem Cell, Cell Press, US, vol. 4(5), May 1, 2009, pp. 381-384.

Web page titled: bioptome.com—Scholten Surgical Instructions; downloaded from <http://www.bioptome.com/pages.php?pages=Products>, 2001, first date of publication unknown, printed on Nov. 1, 2005.

* cited by examiner

METHOD FOR THE ISOLATION AND EXPANSION OF CARDIAC STEM CELLS FROM BIOPSY

This application is a National Phase application of International Application No. PCT/IT2004/000421, filed Jul. 29, 2004, which claims priority of Italian patent application No. RMA2003000376, filed Jul. 31, 2003. The contents of the preceding applications are hereby incorporated in their entireties by reference into this application.

Throughout this application, various publications are referenced. Disclosures of these publications in their entireties are hereby incorporated in their entireties by reference into this application in order to more fully describe the state of the art to which this invention pertains.

FIELD OF INVENTION

The invention concerns a method for the isolation and expansion of cardiac stem cells derived from postnatal cardiac tissue biopsy.

The invention deals with a method for the isolation, expansion and preservation of cardiac stem cells from human or animal tissue biopsy samples to be employed in cell transplantation and functional repair of the myocardium or other organs.

The cells may also be used in gene therapy, for treating genetic cardiomyopathies by expressing the healthy gene in cells from biopsies of subjects with genetic defects, propagating the cells in vitro and then transplanting them in the patient; for treating ischemic heart diseases by inducing the release of angiogenetic growth factors by the transplanted cells; and for the setting of an in vitro models to study drugs.

PRIOR ART

Stem cells (SC) are able to replicate and to differentiate in response to appropriate signals, thus enabling the formation or regeneration of specialized tissues.

It was thought that cardiomyocytes were terminally differentiated cells; however, emerging evidence has shown the modest potential of these cells to proliferate in animal models and in heart transplant patients (1-4).

The limited ability of adult cardiomyocytes to undergo mitosis and to regenerate the myocardium after injury leads to a permanent deficiency in the number of functioning cells, with the development and progression of cardiac insufficiency. In the end stage of the disease, the alterative treatment to transplantation is the implantation of SC in the injured myocardium (cardiomyoplasty). This method has produced promising results in animal models and has been experimented also in humans. However, the problem of having a source and an availability of SC remains (5-7).

While embryonic SC (undifferentiated cells from the embryo that can produce a wide range of specialized cells and that can be derived from the cell mass inside blastocytes which, in humans, form 4-5 days after fertilization of the ovum) have a marked capability to proliferate and differentiate, their potential immunogenicity, arrhythmogenicity, and ethical issues in particular, have limited their use. Moreover, embryonic SC are pluripotent, consequently their use carries a potential risk of generating teratomas (as occurs in animal models). Hence, before these cells can be used, they need to be differentiated in vitro in cardiomyocytes.

There exist various types of cardiomyocytes (ventricular, atrial, sinus node, Purkinje, with pacemaker functions, etc.). Embryonic SC have the potential capability to generate these cardiomyocyte phenotypes in vitro but the yield is insufficient. Furthermore, the in vivo proliferative capability of cardiomyocytes derived from embryonic SC appears to be limited by the growth of multinucleate cells.

An alternative is to use adult SC (undifferentiated cells found in differentiated tissue that are able to proliferate, reproduce and differentiate into the specialized cell types of the tissues whence they were isolated) preferably obtained from the same patient, which would afford the advantage of allowing autologous transplantation without the need for immunosuppressive therapy. For this purpose, skeletal myoblasts (satellite cells) have been employed; however, they differentiate into skeletal myocytes with morphologic and functional properties differing from those of the cardiac muscle. The inability of skeletal myoblasts to transdifferentiate into cardiomyocytes and to couple with them could give rise to arrhythmias or other anomalies SC derived from bone marrow offer an attractive alternative. Mesenchymal SC (MSC) of the bone marrow can differentiate into cardiomyocytes in vitro (treated with DNA-demethylating agents) and in vivo where, however, in the presence of fibrosis, they mostly generate fibroblast-like cells. Hematopoietic SC(HSC) of the bone marrow (so-called side population cells [SPcells]) are pluripotent in that they can generate vascular epithelium, smooth muscle cells and cardiomyocytes. But the functional and electrophysiologic properties of HSC- and MSC-derived cardiomyocytes are not well characterized, and the use of undifferentiated cells instead of cardiomyocytes could give rise to in vivo differentiation into fibroblasts rather than muscle cells or to the development of tumors.

Although human cardiomyocytes have been conventionally considered terminally differentiated cells (i.e. unable to re-enter the cell cycle and to divide), indirect evidence accumulating over the past two years has suggested the existence of adult SC in the heart. These cells are ideal candidates for cardioplasty in that they need no reprogramming, give rise only to cells present in the heart, i.e. cardiomyocytes and vessels (endothelial cells and smooth muscles) and may, because this is their physiologic function, survive in transplant patients, integrate into the surrounding tissues and carry out their functions for longer periods without causing any damage. Patent applications WO 03/008535 and WO 03/006950 concern methods to derive cardiomyocytes from embryonic SC. Patent applications WO 02/13760 and WO 02/09650 deal with the use of adult SC particularly hematopoietic and/or cardiac cells, without indicating a method to isolate them, also in combination) to repair cardiac injury or in treating cardiovascular diseases in general.

Patent application WO 99/49015 deals with the isolation of pluripotent cardiac SC of the adult p53−/− mouse. In particular, the description concerns the heart-derived pluripotent SC that differentiate and proliferate to produce a variety of cell types, including cardiocytes, fibroblasts, smooth muscle cells, skeletal muscle cells, keratinocytes, osteoblasts and chondrocytes. The cells may be employed in methods to treat patients with cardiac tissue necrosis. The SC proliferate and differentiate to produce cardiocytes that replace the necrotic tissue.

However, the method differs from that of the present invention, which was based on the assumption that the cardiac muscle cells, the striate muscles and the smooth muscle cells derived from a common precursor, the myoblast. Furthermore, there is no in vivo evidence from cardiomyopathic animals that supports the applicability of the method. Lastly, the methods differ substantially. In the method described in patent WO 99/49015, adult p53−/− mouse hearts are fragmented, dissociated with DNAse and collagenase. After centrifugation, the sediment myocytes are isolated on a discontinuous gradient (Percoll) and plated on a medium containing 5% FBS and then on a medium containing 15% FBS 20 days later. Between days 20 and 26, small (<5 µm) round, nonadherent, slow-growth, phase-bright cells with a high nucleus-to-cytoplasm ratio form in the suspension. These cells continue to live in the suspension for about 1.5 months in the presence of 10% horse serum. Then the cells remain suspended also without the addition of horse serum. The nonadherent SC do not form colonies in methylcellulose and proliferate in the presence of serum, SCF, aFGF, bFGF, and cFGF. In the absence of horse serum, the nonadherent cells differentiate into differently appearing adherent cells the authors have identified by mainly morphologic criteria as cardiocytes, chondrocytes, fibroblasts, smooth muscle cells, skeletal muscle myoblasts, pericytes, and other cells the authors have called adherent SC. About one fourth to one fifth of these cells is positive to alkaline phosphatase (osteoblasts and endothelial cells); all cells are negative to acetylated LDL (absence of endothelial cells) and to myosin heavy chain (MF20). The cells undergo mitosis when stimulated by bFGF, aFGF and cFGF. In the absence of serum, they differentiate into cells resembling a fried egg (myocytes). After treatment with ascorbic acid/α-GP, they differentiate into chondrocyte-like cells.

Adherent cells cloned by limiting dilution give rise to mesenchymal cells, including osteoblasts, chondrocytes, adipocytes and myocytes, although they cannot be clearly identified due to often inappropriate morphologic criteria and markers. All the cells tested negative to acetylated LDL (absence of endothelial cells). None of the 11 isolated clones could be induced to differentiate toward a single mesenchymal lineage.

The isolation of the cardiac-derived SC of neonate mice (1-4 days) is also described, wherein the passage of myocytes on human fibronectin is added to eliminate the fibroblasts. However, no data are given about the characteristics of the isolated SC. Furthermore, the cells isolated with the previous method do not give rise to the formation of an essential component of the heart tissues, i.e. vessels and endothelium.

DESCRIPTION OF THE INVENTION

The method of the present invention employs heart biopsy tissue as starting material, hence an elective material that cannot be used in the method described in patent application WO 99/49015, since the material was insufficient. After fragmenting the biopsy specimen and possibly using dissociating agents (e.g. trypsin, EDTA and collagenase), the fragments are plated and added to a medium containing 10% FBS; 10-30 days later, fibroblast-like adherent cells grow from the explants over which small round, phase-bright cells migrate that tend to cluster but are either not or only weakly adherent. The cells are isolated by washing and mild dissociation (e.g. EDTA, trypsin-EDTA for 2-3 min). The cells are then plated on polylysine-treated cellular substrates in an appropriate medium unlike that used in the previous technique, in that it is horse-serum-free and contains other growth factors; after 2-3 days cell aggregates (cardiospheres) arise that tend to grow as floating formations. The authors have found that the cardiac-forming cells are postnatal SC that can be advantageously employed for reimplantation in the myocardium.

These cells are able to multiply, while maintaining their origin characteristics for a period (at least 60 days) that is long enough to markedly enrich the cell population. Mechanical disaggregation of the cardiospheres (CS) by repeated pipetting and changing the medium every 3 days increases the number of CS (about 100-fold every 10 days) for at least the first 20 days. Given the number of SC that can be derived from a biopsy and their ability to multiply in vitro, it is thought that they can be used to replace a greater amount of tissue than that removed.

Certain cells in the CS present stem-cell markers (ckit, sca-1, CD34) that are able to differentiate toward the main components of the myocardium (cardiomyocytes and vessels). As evaluated by immunohistochemistry and/or RT-PCR, certain cells spontaneously express, particularly at the border of the CS, markers for cardiomyocyte (troponin I, ANP, myosin heavy chain) and for endothelial cells (von Willebrand factor and Ve-cadherin). The human CS, in a co-culture with rat myocytes, beat spontaneously. When inoculated subcutaneously in SCID mice, the murine CS give rise to growths containing cardiac muscle tissue and vessels within several days. The authors have thus demonstrated that the SC can be derived in a reproducible manner from biopsy tissue of the atrium, ventricle and auricola of human subjects aged from 1 month to 70 years. The CS pertaining to the invention can be cryopreserved, and they maintain their functional characteristics after thawing.

Adult cardiac SC with similar characteristics can also be isolated from the mouse. In particular, to better understand cell differentiation in CS, several breeds of transgenic mice were studied; the findings confirmed the results obtained with human cells. Lastly, the authors have shown in an animal model that human CS can be used for cardioplasty. When inoculated in the infarcted area (transthoracic cauterization or LAD ligation) of a SCID mouse, the cells give rise to cardiac tissue that presents good integration with the host tissue, as observed by morphology and immunohistochemistry studies.

Hence, the isolation and expansion of CS by the method of the invention is novel and advantageous compared with that described in the previous technique in terms of the origin of the sample, the methods of isolation and expansion and the morphologic and functional characteristics of the derived cells.

DETAILED DESCRIPTION OF THE INVENTION

The method comprises the following steps: biopsy sample obtained under sterile conditions and transported to the laboratory; preparation of fragments sized large enough to allow diffusion of nutrients present in the culture medium; distribution of fragments on culture plates and incubation under conditions appropriate for cell survival and growth; sampling of culture medium and cells and transfer to other culture plates under conditions adequate for cell expansion.

An object of the invention is a method to obtain stem cells able to repair damaged myocardiac tissue, comprising the following steps:
a) take a biopsy specimen of cardiac tissue and keep it in an appropriate culture medium;
b) treat the specimen under appropriate conditions with mild mechanical and/or chemical and/or enzymatic techniques to obtain tissue fragments sized large enough to allow the diffusion of nutrients present in the medium;
c) leave the tissue fragments to adhere to appropriate solid supports and maintain them in a medium containing convenient serum and/or growth factors;
d) allow the cells to grow, changing the medium partially or completely, until multicellular structures form that are either weakly adherent or do not adhere to the support;
e) separate said multicellular structures from the rest of the culture;

f) treat said multicellular structures by mild dissociation until most of the small phase-bright spherical cells detach but maintain their morphologic and functional characteristics;

g) plate the cells on culture substrates treated with polylysine or other agents promoting the adhesion of the culture to the support in a medium containing at least the minimal essential constituents for the growth of mammalian cells;

h) possibly repeat steps d) to g) at least once;

i) select the cells that aggregate in phase-bright spheroid formations (cardiospheres);

l) electively promote the formation of new cardiospheres by mild dissociation thereof and new formation;

m) eventually cryopreserve the cardiospheres for use after thawing.

Preferably stem cells are derived from non-embryonic cardiac tissue biopsies.

In one embodiment of the invention at least one of the steps follows treatment with oxygen concentrations different from that normally present in the atmosphere in order to modify the biologic characteristics of the cultures.

Experts in the field will understand that the CS derived with the procedure of the invention may be able to generate continuous cell lines following spontaneous transformation or transformation induced by chemical, physical or biologic agents.

In another embodiment the cells giving rise to and/or constituting cardiospheres are fused with other cells.

In another embodiment the cells giving rise to and/or constituting cardiospheres are used for nuclear transfer to and from other cells.

In another embodiment the cells giving rise to and/or constituting cardiospheres are grown in at least one stage on biodegradable and/or biocompatible supports.

In another embodiment the cells giving rise to and/or constituting cardiospheres are cultured in bioreactors and/or fermenters.

It is another object of the invention cells giving rise to and/or constituting cardiospheres able to repair myocardiac tissue obtainable according to the method of previous claims. Preferably said cells are to be used in gene therapy. Preferably said cells are to be used for nuclear transfers to and from other cells. The CS derived with the method of the invention can be variously used in the repair of myocardiac tissue, for nuclear transfer from and to other cells, in gene therapy for cardiopathies of genetic origin.

METHODS AND MATERIALS

Tissue Samples

Figure 1:
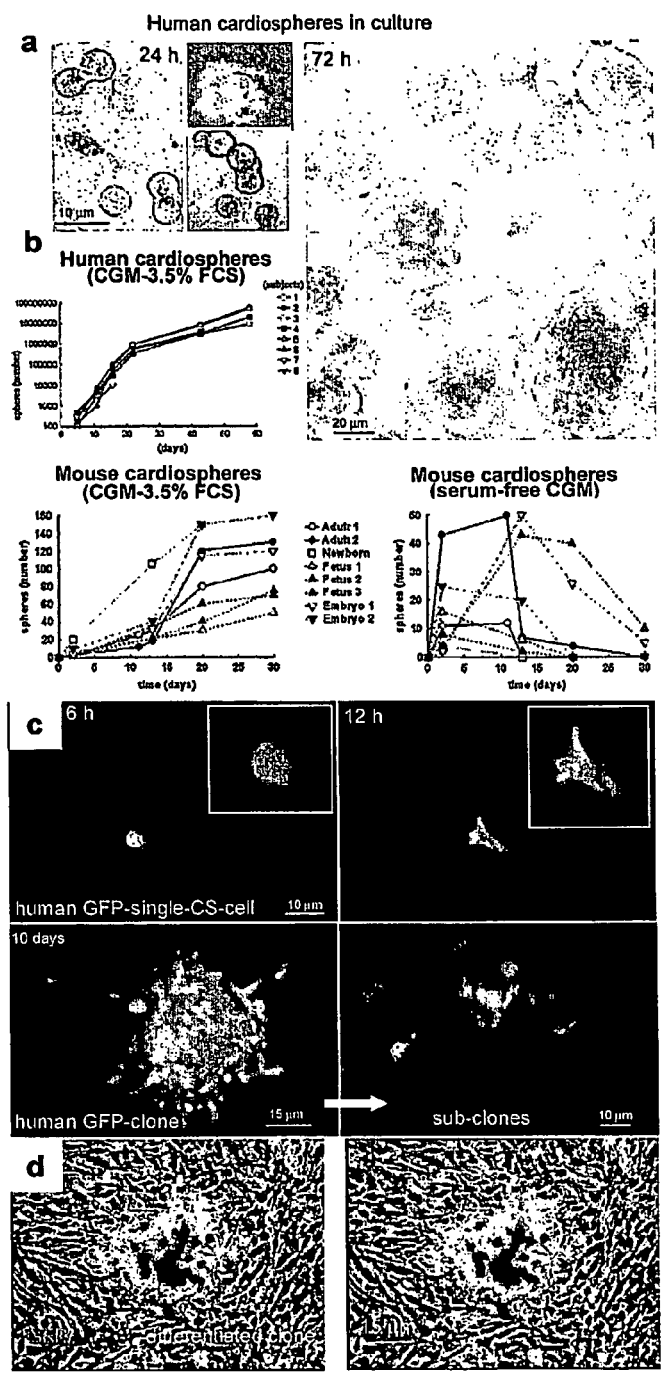
FIG. 1—CS proliferation. a, Phase micrograph of floating CSs (cultured from <24 h to >48 h) derived from primary culture of a human atrial bioptical sample. b, Proliferation curves of human and mouse CSs [derived from 8 different subjects (top) and from pre- and post-natal hearts (bottom) respectively], in the presence (left) and in absence (right) of 3.5% serum. Number of spheres refers to the mean number per well from which 90% of the spheres where withdrawn at each time-point for further analysis. Note the different pattern of proliferation between the human and mouse CSs and the rapid rise of the curves, followed by an irreversible decline in the serum-free conditions. c, Fluorescence analysis of a single cell (upper-right) (obtained from a dissociated GFP-expressing CS), when plated by limiting dilution on mitomycin-treated STO-fibroblast-coated 96-wells plates in CGM, over the course of the generation of the GFP-labeled clone. This clone could be passaged and expanded on poly-D-lysine coat (lower-left). d, x-Gal staining of a eGFP/MLC3F clone (obtained as those human) after 48 hours exposure of growth factors-free medium: in these conditions cells in the clone become more flattened with many nuclei showing a blue color, demonstrating that a differentiation process occurred.

The human tissue came from myocardiac biopsies of adult or other patients who underwent open heart surgery (aortocoronary bypass, cardiac valve replacement, tetralogy of Fallot, ventricular septum defect) or heart transplantation for advanced dilated cardiomyopathy or post-infarction chronic congestive cardiomyopathy. The murine tissue came from the hearts of previously characterized homozygous MLC3F-nLacZ mice (8) homozygous troponin-I-nLacZ (9) and EGFP/ckit (10) CD1-crossed mice. The mice show localized nuclear expression (cardiac and skeletal) of the transgene for β-galactosidase of the myosin light chain promoter, a tissue-specific nuclear expression (exclusively cardiac) of the transgene for troponin-I and a cytoplasmic expression of the EGFP transgene of the ckit promoter (the gene in these cell experiments), respectively. B5-EGFP mice (11), which show generalized expression of cytoplasmic GFP, were used as base strains. The crossed MLC3F-nLacZ/EGFP, MLC3F-nLac-Z/EGFP-ckit, Tn-I-nLac-Z/EGFP-ckit mice were bred according to experimental protocol. The human cardiac tissue biopsies were preserved in serum-free IMDM (Euroclone) at 0° C. and maintained at this condition until arrival in the laboratory (within 2 h).

Processing, Isolation and Cryopreservation of Sphere-Forming Cells

After careful dissection of the macroscopically visible connective tissue, the samples were cut into 1-2 mm³ pieces, washed 3 times with $Ca^{++}/Mg^{++}$-free phosphate buffered solution (PBS, Invitrogen) and sequentially digested 3 times for 5 min each at 37° C. with 0.2% trypsin (Gibco) and 0.1% collagenase IV (Sigma). The obtained cells, the bulk of which are elements of contaminating blood, were discarded and the remaining tissue fragments were washed with complete explant medium (CEM) [IMDM supplemented with 10% fetal calf serum (FCS) (Hyclone), 100 mg/ml penicillin, 100 U/ml streptomycin (Gibco), 2 mM L-glutamine (Gibco), 0.1 mM 2-mercaptoethanol (Sigma). The tissue pieces were then fixed to Petri dishes (Falcon) by light scraping with a scalpel on a plastic surface. The explants with cultured at 37° C. in 5% $CO_2$ in complete IMDM. The murine cardiac tissues were treated similarly, except for the embryonic hearts, where enzyme digestion prior to explant digestion was omitted and the organs were partially dissociated with a 25 gauge needle. After a period of 1 to 3 weeks (depending on the origin of the sample, i.e. a shorter period for the embryonic tissue and a longer one for the adult tissue), a layer of fibroblast-like cells forms that derive from or surround the explants. The explants are then periodically treated (every 6-10 days, 4 times maximum) to isolate the sphere-forming cells. To remove only the phase-bright cells, which migrate from the explants to the outer cell layer, the medium is removed, and the material is collected by washing it twice with $Ca^{++}$—$Mg^{++}$-free PBS and once with 0.53 mM EDTA (Versene, Gibco) for 1-2 min, followed by mild trypsinization with 0.5 g/L-0, 53 mM Trypsin-EDTA (Gibco) at room temperature for another 2-3 min under visual microscopy control. After the cells are collected, complete medium is added to the explants, whereas the cells obtained by washing and enzymatic treatment are collected by centrifugation (1200 rpm for 7 min) and resuspended in cardiosphere-growing medium (CGM) (35% complete IMDM/65% DMEM-Ham's F-12 mix with 2% B27 [Gibco], 0.1 mM 2-mercaptoethanol, 10 ng/ml EGF (Prepotek EC, Ltd.), 40 ng/ml bFGF (Prepotek EC, Ltd.), 4 nM cardiotrophin-1 (RD), 40 nM thrombin (Sigma) (final concentrations), antibiotics and L-Glu as in the complete medium. Depending on the number of cells obtained (from $10^4$ to $4 \times 10^5$ cells/explant), the cells were resuspended by repipetting them and then plating about $2 \times 10^5$ cells/ml on poly-D-lysine (BD) coated multi-well plates. After 12-24 h, several cells begin to divide and after 48 h, cell groups form that are often surrounded by a thin membrane and that can grow as floating spheres and adherent spheres. The growth medium is partially changed every 2-3 days, and the spheres are mechanically triturated using a pipette or 1 ml needles. For cryopreservation, the spheres (washed in $Ca^{++}$—$Mg^{++}$-free PBS and Versene) are resuspended in the freezing medium (complete IMDM/DMEM-Ham-F-12 50: 50, 5% B27, 10% DMSO). To calculate the growth curves, all the spheres are counted during the first week of growth, and then 90% of the spheres are removed at defined times (and used for RT-PCR or immunohistochemical analysis); after adding CGM and mechanically triturating the residual spheres, they are left to proliferate until the next sampling, when they are recounted. BrdU labeling is performed for 12 h on the newly generated spheres and at defined times in the other spheres, as indicated (Roche). For clonal analysis, the human CSs are infected with a third-generation lentiviral vector, pRRLsin-.PPT-PGK.GFP expressing green fluorescent protein (GFP), as described elsewhere (12). After being washed twice, the GFP-labeled CSs are dissociated into single cells by trituration in $Ca^{++}/Mg^{++}$-free PBS, Versene, and 1× trypsin-EDTA solutions in sequence, resuspended in CGM, and then seeded at a presumed concentration of 1 cell/well in 96-well plates coated with a feeder layer of mitomycin-C-treated STO fibroblasts (2 μg/ml). For differentiation on a substrate-coated surface, $Ca^{++}/Mg^{++}$-free PBS-washed, centrifuged and partially dissociated CSs are repeatedly pipetted and then seeded in a small volume of CEM (200-300 μl) on type I collagen-(Sigma) or Matrigel-(Falcon) coated dishes and cultured for 3-6 days.

In Vivo Analysis

For heterotopic transplantation, about 60 pooled CS obtained from pre- and postnatal EGFP/MLC3F-nLacZ or EGFP/TnI-nLacZ or MLC3F/nLacZ, TnI-nLacZ mice were washed twice in PBS and suspended in 100 µl of Matrigel (BD) and subcutaneously injected into the dorsal region of anesthetized (ketamine, 35 mg/kg i.m) adult NOD-SCID mice. Transplanted-cardiosphere survival and function were monitored by direct palpation of beating through the skin. After about 3 weeks, the mice were sacrificed and the isolated inoculum was embedded in OCT for immunocytochemical analysis. After thawing, 10-day cultures of cryopreserved human CS derived from ventricular and atrial cardiac explants from adult subjects were used for orthotopic transplantation. About 20 washed and partially dissociated CS were suspended in 3 µl PBS and injected in the infarcted myocardiac area using a 27 gauge needle and a Hamilton syringe. Myocardiac infarction was induced as described elsewhere (13) with slight modifications. Briefly, the recipient NOD-SCID mice (anesthetized with ketamine [35 mg/kg]+xylazine [5 mg/kg] i.p.) underwent transthoracic cauterization (Surgitron 140 v) with a modified electrocautery probe inserted through the internal intercostal muscle in the fourth intercostal space on the anterior surface of the heart. Electrocauterization (ca. 40 W) was applied twice for 1 sec in the cutting mode before the CS were injected (the same volume of PBS was injected in the control mice). In some mice myocardial infarction has been also induced by LAD ligation. After about 3 weeks, the mice were sacrificed and the isolated heart was embedded in OCT after extensive washing in PBS and fixing with paraformaldehyde (4%) in PBS pH 7.4.

Immunocytochemistry

Immunocytochemistry on tissue sections and on cell cultures was performed as described elsewhere (14) using the following antibodies: monoclonal anti-human-cTnI, anti-human-cardiac-MHC, anti-human nucleus and polyclonal (pAb) anti-human ANP (Chemicon); mAb anti-CD-31, CD-34 (BD Biosciences), mAb anti-human Cripto-1 (RD), monoclonal anti-Ve-cadherin, anti-sca-1, mAb anti-mouse-cKit (Pharmigen), mAb anti-human-c-Kit (DAKO); pAb anti-human-von-Willebrand-factor and mAb anti-human-KDR (Sigma); mAb MF20 and pAb anti-mouse/human MHC (14), anti-desmine and anti-Smooth-Muscle-Actin (Sigma), mAb anti-human/mouse-cTnI (15), donated by S. Schiaffino (Dept. of Pathology, Univ. of Padua), pAb anti-mouse-flk-1 (Santa Cruz, USA). β-galactosidase activity was detected by light microscopy, as described elsewhere (14).

Reverse-PCR Transcription Analysis

Reverse-PCR transcription analysis was performed as described elsewhere (16). The oligonucleotides for amplifying the genes of the CS derived from the pediatric (pCS), adult subjects (aCS) and heart fragments (H) were the following:

```
hNkx2,5 (150 bp) forw
5'-CTCCCAACATGACCCTGAGT-3'
and rev
5'-GAGCTCAGTCCCAGTTCCAA-3', hANF (350 bp) forw
5'-AATCAAGTTCAGAGGATGGG-3'
and rev
5'-AATGCATGGGGTGGGAGAGG-3',
```

```
hVe-Cad (330 bp) forw
5'-TCTCTGTCCTCTGCACAA-3'
and rev
5'-ATGCAGAGGCTCATGATG-3', hGAPDH forw
5'-GAAGAGCCAAGGACAGGTAC-3'
and rev
5'-CTGCACCACCAACTGCTTAG-3;
```

The oligonucleotides for amplifying the genes of the murine CS and the heart fragments (H) were the following:
mMHC (302 bp) forw 5'-GAAGAGTGAGCGGCGCAT-CAAGGA-3' and
rev 5'-TCTGCTGGAGAGGTTATTCCTCG-3',
m α cardiac actin (494 bp)
forw 5'-TGTTACGTCGCCTTGGATTTTGAG-3' and
rev 5'-AAGAGAGAGACATATCAGAAGC-3',
m cardiac TnC (410 bp) forw 5'-AATGGATGACATCTA-CAAAG-3' and
rev 5'-TGAGCTCTTCAATGTCATCT-3'.
mGAPDH forw 5'-CCTCTGGAAAGCTGTGGCGT-3' and
rev 5'-TTGGAGGCCATGTAGGCCAT-3'.

Results

Isolation and Expansion of CS

Sphere-generating cells were obtained by mild enzymatic digestion of explanted human atrial or ventricular biopsies and fetal, embryo and postnatal mouse hearts. Soon after the generation of a layer of fibroblast-like cells from well adherent explants, small, round phase-bright cells began to migrate over this coat. These cells could be harvested periodically by treatment with EDTA and mild trypsinization, and allowed to grow on poly-D-lysine-coated culture surfaces, in a low-serum (3.5% FCS) medium supplemented with a serum substitute (B27), growth factors (EGF and bFGF), cardiothrophin-1 (CT-1) (17) and thrombin (18), which, in the first week of culture, led to a seven-fold increase in the number of spheres with respect to that obtained using the medium supplemented with the others factors either alone or in combination. Time course observations of cells derived from both human and murine explants showed that, early after their seeding (30 min), some of these cells began to divide while still in suspension; most cells became loosely adherent, others remained in suspension and some contaminating fibroblast-like cells attached firmly to the poly-D-lysine coat. Cellular divisions were evident also from the loosely adherent cell population and produced clusters of small, round phase-bright cells [that we termed cardiospheres (CSs)] after 10-12 hours (FIG. 1a). Within 24-36 hours from their appearance, CSs increased in size and some of them detached from the culture surface; after 48-72 hours most CSs were between 20 and 150 µm in size and, when not subjected to mechanical dissociation, the largest contained dark zones within their inner mass (FIG. 1a).

Murine CSs started a spontaneous rhythmic contractile activity soon after their generation and maintained this function during their life span, while human CSs did so only when co-cultured with rat cardiomyocytes. To be sure that contraction was a new trait acquired by the cs cells, gfp-labeled human CSs (partially or totally dissociated) were co-cultured with cardiomyocytes pre-stained or not with dil. Contracting gfp-labeled cells were observed after 48 hours of co-culture; furthermore, from this time onwards, a red color stained also the green fluorescent cells, suggesting that a connection is created between the human CSs and the rat cardiac cells. In fact, labeling of human cs/rat-cardiomyocyte co-cultures (in which only human cells were pre-labeled with gfp by lentiviral infection) with cx-43, the major ventricular gap junction protein, demonstrated the typical punctuate fluorescence pattern along the cytoplasmatic membrane (FIG. 2f), indicating that a functional connection is created between the two cellular populations.

CSs were found to be composed of clonally derived cells and did not simply represent cellular aggregates. In fact, when human CSs [expressing the green fluorescent protein (GFP) after infection with lentiviral vectors expressing the reporter gene] or murine CSs (derived from eGFP/MLC3F or eGFP/cTrI-mice) were dissociated and plated as single cells on mitomycin-treated STO-fibroblast-coated 96-wells or at clonal diluition on 10 cm Ø Petri dishes, fluorescent spheres that could be sub-cloned on poly-D-lysine-coated surfaces (FIG. 1c) were generated with a 1 to 10% efficiency. These sub-clonally derived CSs show the same functional and phenotypic behavior in culture: after 3 days from their appearance, some murine clones started to, and after 48 hours of culture with CEM, the majority (6/7) of these showed expression of the lac-Z transgene within nuclei after specific histochemical staining (FIG. 1d). Equally, human clones, derived from a single GFP-labeled cell, start a synchronous beating and express cTnI after 48 hours of co-culture with rat cardiomyocytes.

Furthermore, when BrdU was added to the culture medium, virtually all cells in the small, and those of the inner part of the largest CSs, were labeled (FIG. 2a), indicating that these cells were newly generated.

Human CS-generating cells were capable of self-renewal. With periodical dissociation, together with partial substitution of the growth medium every 2-3 days, a log-phase expansion of spheres was obtained (FIG. 1b). Growth was slower for mouse CSs (owing, probably, to the more differentiated features assumed in culture such as beating) and, serum-dependent (FIG. 1b) as for the human ones.

As shown in FIG. 2a, confocal immunofluorescence analysis of BrdU labeled human CSS with anti-BrdU (green) and cardiac-troponin i (ctni) or atrial natriuretic peptide (anp) (red), revealed BrdU-positive cells particularly in the inner part of the spheres, while ctni- or anp-positive cells were mainly localized in the external layers. Furthermore, several cs-cells expressed cardiac differentiation markers (ctni, anp) while still dividing, as indicated by BrdU incorporation (FIG. 2a), suggesting that early cardiac differentiation already occurred during the log-phase growth; generally, within 2-3 weeks, some spheres became adherent, showing a more flattened morphology. Some small cells eventually migrated out from these "sun-like" spheres in the form of adherent (differentiated) or small, round cells that could generate new spheres. After thawing from cryopreservation, CSs proliferated again, maintaining their propensity to beat.

Phenotypic analysis of newly developing human and mouse CSs revealed expression of endothelial (KDR (human)/flk-1 (mouse), CD-31) and stem-cell (CD-34, ckit, sca-1) markers. As shown in FIG. 2b, CSs at the 2-10 cell stage, strongly reacted with antibodies against these antigens. In larger spheres, the expression pattern of some of these markers (particulary cKit) was similar to the BrdU labeling (positive staining in the center and in some peripheral zones generating satellite spheres).

Figure 2:
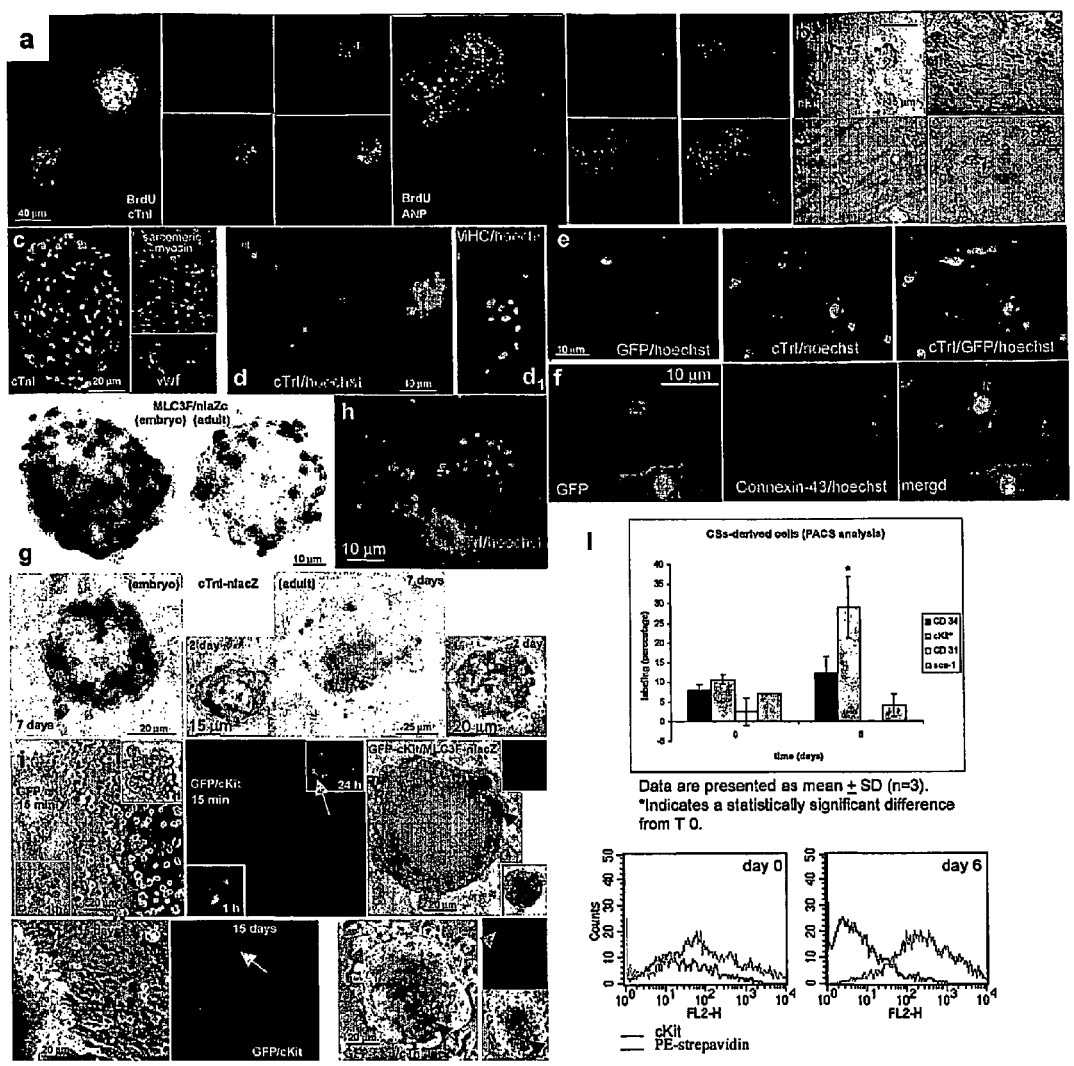
FIG. 2—CS characterization. a, Fluorescence-confocal analysis of BrdU-labeled human CSs for cardiac differentiation markers: 6 µm scans (from the periphery to the center of the sphere) and final pictures (small and large images respectively). BrdU (green), cTnI and ANP (red). b, Confocal analysis of human CSs after 12 h of culture: CD-34, CD-31, KDR and c-Kit labeling of CS-generating cells at the beginning of sphere formation. c, Fluorescence phenotype analysis of human CSs (cryosections): cTnI (red), sarcomeric myosin and vWf (green). d-$d_1$, Fluorescence phenotype analysis of human partially dissociated-CSs, after four days of culture on collagen coat in CEM: cTnI (red) expression appears in the cytoplasm of the human cells (migrated from the sphere) showing a triangular shape with a row arrangement). e, Fluorescence analysis of partially dissociated eGFP-labeled human CSs at 96 h of co-culture with rat cardiomyocytes: the same green cells that showed a synchronous contraction with cardiocytes, express cTnI. f, Fluorescent analysis of connexin-43 expression (red) in eGFP-labeled human CSs co-cultured with rat cardiomyocytes (as in panel e): a punctuate red fluorescence is present in the cell membrane of human cells. g, Phase micrograph of CSs from MLC3F-nlacZ and cTnI-nlacZ mice: nuclear lacZ expression mainly localized in the external layers of both embryo and adult CSs, after a short time from their formation (inserts) and after a few days of culture (right and central panels). Nuclei of cells (derived from partially dissociated CSs, cultured for 5 days on collagen-coated surfaces) are also blue stained. h, Florescence analysis of a spontaneously differentiated mouse CS: as suggested from the synchronous contraction showed in culture, cTnI (red) is expressed in the sphere and the cells migrated; in the last, sarcomers are also evident. i, Fluorescence and phase analysis of CSs from GFP-cKit, GFP-cKit/MLC3F-nLacZ and GFP-cKt/cTnI-nlacZ mice. GFP-labeled cells were present a few minutes after their seeding in culture with CGM, at the beginning of the generation of the CSs, later in their inner mass and after their migration out from the oldest adherent spheres (arrows) (upper lower and left and central panels). GFP-labeled cells did not co-localize with the blue-stained ones (arrows) in CSs from GFP-cKit/MLC3F-nLacZ and GFP-cKt/cTnI-nlacZ mice; fluorescent cells were present also in the CSs' growth area (arrows) (right upper and lower panels). Fluorescence, phase (small) and merged (large) images. l, FACS analysis of post-natal mouse CSs-derived cells. A time course at 0 and 6 days was performed and the phenotype profile for CD34, cKit, Cd31 and sca-1 expression was analyzed and showed as percentage of positive events. Data are presented as mean±SD (n=3). *Indicates a statistically significant difference from T 0.

A time course (0 and 6 days) of the quantitative characterization of CSs cells with these stem and endothelial markers was performed by FACS analysis (FIG. 2 1: as shown, at the beginning of their formation (T 0) the phenotype of these cells seems to reflect the epi-fluorescent microscopy analysis with about 10% of positive staining for all four phenotypes. However, at 6 days (T6) cKit appears as the only conserved marker, suggesting that the cKit$^+$ cells could be the main ones contributing to the maintenance of proliferation, while the initial positivity to the others may reflect an early activation state, as has been indicated for CD-34 in several system (19). Fluorescence microscopy analysis, performed on cryo-sectioned human CSs revealed expression of cardiac-differentiation markers (cTnI, MHC) and also of endothelial markers [von Willebrand factor (vWf)] (FIG. 2c). When totally or partially dissociated into single-cells and cultured on collagen-coated dishes, in the same medium as the explants, mouse and humans CS-derived cells assumed a typical cardiomyocyte morphology, phenotype (fig. d-d$_1$, h) and function documented (in the mouse only) by spontaneous contraction.

As aforementioned, human CSs did not beat spontaneously; however, these began to beat within 24 h when co-cultured with postnatal rat cardiomyocytes, losing, after this time, their spherical shape and assuming a "sun-like" appearance. Markers of cardiac differentiation were co-expressed within GFP in human labeled CSs-cells (FIG. 2e).

To follow the differentiation process of CSs during the pre- and post-natal age, MLC3F-nlacZ and cTnI-nlacZ mice were utilized (8, 9). These mice express a form of lacZ transgene that localizes within the nucleus under the skeletal and cardiac muscle myosin light chain or cardiac troponin I promoter, respectively. CSs obtained from embryonic day 9-12, fetal day 17-18, neonatal and adult mice, showed spontaneous expression of the reporter gene in a variable percentage (10-60%) of spheres in the different culture conditions employed (FIG. 2e); moreover, as for the human ones, CS-generating cells from mice expressed stem (CD-34, sca-1, cKit) and endothelial cell markers (flk-1, CD-31).

On this basis, we utilized transgenic mice expressing the green fluorescent protein (GFP) under the control of the c-kit promoter (10), in order to further clarify the cellular origin of these spheres and to follow the pattern of their growth process. As shown in FIG. 2i, GFP-positive cells were present from the beginning of the formation of the CSs and, albeit with reduced fluorescence intensity, also later, within the mass of cells of the CSs and in cells migrating from old "sun-like" adherent CSs. Moreover, as suggested by the growth pattern of human CSs, when satellite secondary CSs appeared to detach from the primary ones, GFP-positive cells localized on the margins of the latter and in the inner part of the former.

We studied this process in double-heterozygous mice obtained from GFP-cKit/MLC3F-nlacZ or GFP-cKit/cTnI-nLacZ crossings: as shown in FIG. 2i, beta-Gal-positivity did not co-localize with GFP in cells present within the growing areas.

In conclusion, CSs appear to be a mixture of cardiac stem cells, differentiating progenitors and even spontaneously differentiated cardiomyocytes. Vascular cells were also present, depending on the sphere's size and time in culture. It is possible that, as for neurospheres (20), differentiating/differentiated cells stop dividing and/or die while stem cells continue to proliferate in an apparent asymmetric way, giving rise to many secondary spheres and to exponential growth in vitro. Mechanical dissociation favors this process. Death, differentiation and responsiveness to growth factors of the different cells within the CS, could depend on its three-dimensional architecture and on localization within the CS (21-22). The spontaneous formation of spheres is a known prerogative of neural stem cells, some tumor cell lines (LM) (22), endothelial cells (23) and fetal chicken cardiomyocytes (24). All these models (ours included), that mimic the true three-dimensional architecture of tissues, consist of spheroids of aggregated cells which develop a two-compartment system composed of a surface layer of differentiated cells and a core of unorganized cells that first proliferate and thereafter disappear over time (perhaps through apoptotic cell death). As well documented in fetal chick cardiomyocytes and endothelial cell spheroid culture, three-dimensional structure affects the sensitivity of cells to survival and growth factors (22, 23). In particular, central spheroid cells do not differentiate and are dependent on survival factors to prevent apoptosis, while the cells of the surface layer seem to differentiate beyond the degree that can be obtained in two dimensional culture and become independent of the activity of survival factors. Furthermore, cell-cell contact and membrane-associated factors are known to be important for the division of neural precursor cells (25), in accordance with the notion that stem cells will only retain their pluripotency within an appropriate environment, as suggested by the "niche" hypothesis (26).

To investigate the survival and morpho-functional potential of the CSs in vivo, two sets of experiments were performed: in the first, CS cells were injected in the dorsal subcutaneous region of SCID mice; in the second, they were injected into the hearts of SCID-beige mice, acutely after myocardial infarction. The intention of ectopic transpantation experiments was to study the pattern and the behavior of growth of CSs in a neutral milieu (i.e. one without specific cardiac induction), in order to verify their unique potential of generation of the main cardiac cell types and to exclude the possibility of neoplastic transformation. For these experiments about 60 pooled spheres/inoculum/mouse from pre- and post-natal MLC3F-nlacZ/B5-eGFP TnI-nlacZ/B5-eGFP mice or MLC3F-nlacZ/CD-1 and cTnI-nlacZ/CD-1 mice, were employed. During the first 10 days, beating was appreciable through the skin over the injection site, distant from large blood vessels. On day 17, animals were sacrificed and the inoculum recognized as a translucent formation, grain-like in size, wrapped in ramified vessel-like structures. Observation of unfixed cryosections by fluorescence microscopy revealed the presence of open spheres from which cells appeared to have migrated; clusters of "black holes", particularly in the periphery of the structure, were evident. The tissue contained tubular formations, surrounded by nuclei (Hoechst-positive), identified as cardiac sarcomeres because they were positive for cTnI and sarcomeric myosin (FIG. 3a). Alpha-SMA-positive structures (known to be transiently expressed during cardiomyogenesis (27)), were present in the remainder of the spheres and associated with the vasculature (the clusters of "black-holes"): this exhibited well-differentiated structures with a thin endothelium expressing Ve-cadherin (FIG. 3a) and a relative large lumen containing erythrocytes, indicating the establishment of successful perfusion by the host. Light microscopic observation of the inoculum, after X-Gal staining, showed strong nuclear expression of striated muscle-specific lacZ in the remainder of the spheres and in some cells close to them. No multi-differentiated structures suggesting the presence of tumor formation were observed.

Figure 3:
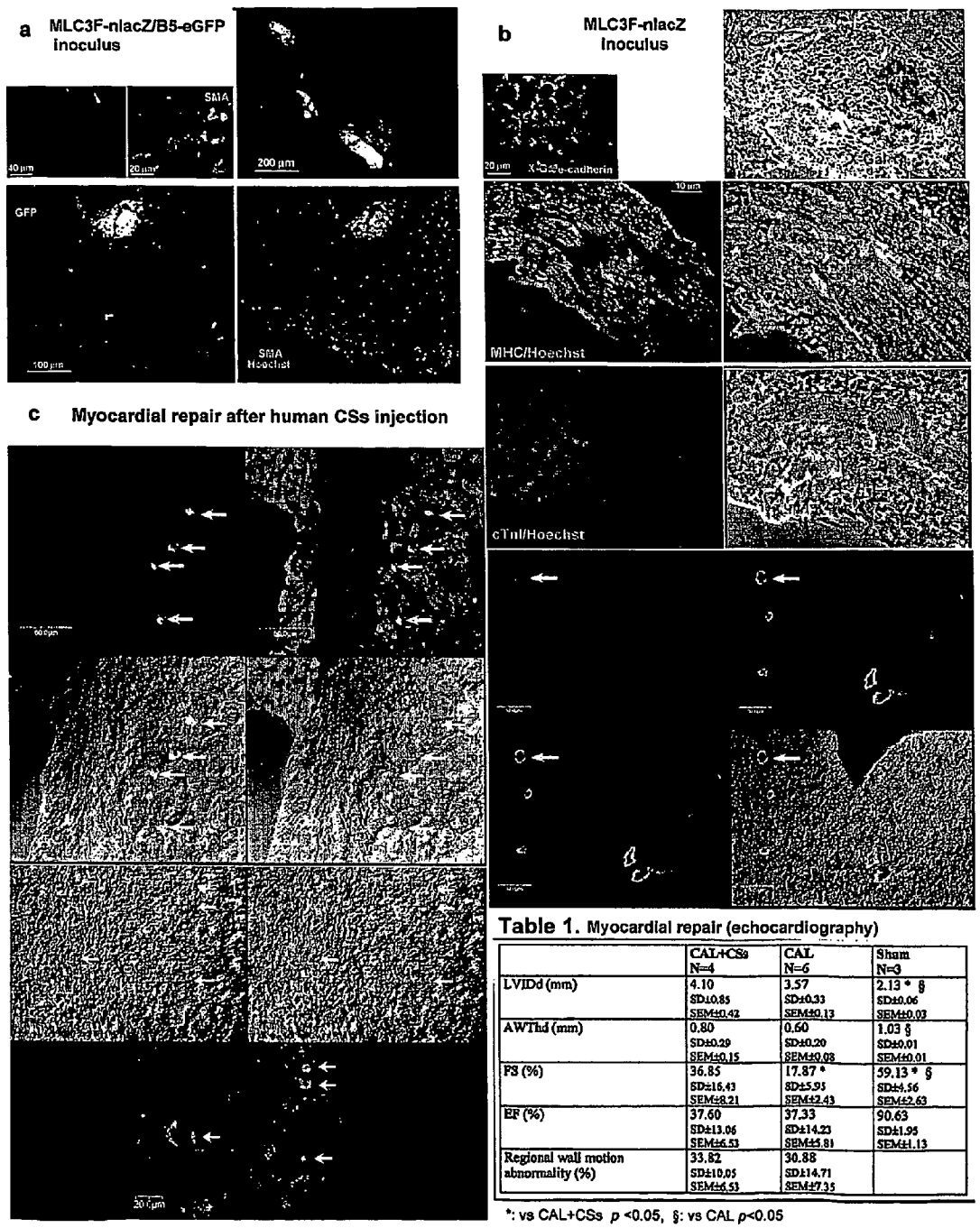
FIG. 3—In vivo analysis. a, Ectopic transplantation in SCID mouse of CSs from MLC3F-nlacZ/B5-eGFP mouse (upper left panels). Fluorescence analysis of unfixed cryosections (upper left small, upper right and down left large images) from the subcutaneous dorsal inoculum (day 17): GFP-cells seemed to have migrated from the spheres while clusters of vessel-like structures could be observed mainly in the external area (insert). Staining for SMA of one of these cryosections showed positive immunoreaction of the sphere and some cells within the inoculum. b, Fluorescence (right) and phase analysis (left, merged) of fixed and immunostained cryosections from dorsal inoculum of CSs from MLC3F-nlacZ/CD-1 and cTnI-lacZ/CD-1 mice: tubular structures were stained for sarcomeric myosin and cTnI (middle and lower panels respectively). X-Gal staining labeled the cells within and those migrating from a CS (upper right). Endothelial markers (SMA and Ve-cadherin), stained the vasculature ("black-holes") (small images). c, Orthotopic transplantation on a SCID-bg mouse, of cryopreserved human CSs into the viable myocardium bordering a freshly produced infarct. Confocal analysis of cryosectioned left ventricular heart after 18 days from the coronary ligature, shows that (upper left panel) cardiomyocytes expressing MHC (red) in the regenerating myocardium (particularly those indicated by the two central arrows), stain positive also for lamin A/C (green) (a specific human nuclear marker). In these cells MHC expression is evident mainly in the perinuclear area. Lamin A/C-labeled cells (red) are present in newly generated capillaries staining for smooth α-actin (upper right panel), and PECAM (down left panel); connexin-43 (red) (down right high magnification panel), as in the co-culture experiments, lines cytoplasmatic membrane of some human cell (green) in the regenerating myocardium. Table 1. Effect of human CSs ortotopic transplantation on echocardiographic index of myocardial performance. Data are presented as mean±SD. Abbreviations: LVIDd, left ventricular internal dimension at end diastole; AWThd, anterior wall thickness; FS, fractional shortening; EF, ejection fraction. *: vs CAL+ CSs p<0.05, §: vs CAL p<0.05

To test the acquisition of functional competence and the cardiac regenerative potential of the CSs when challenged into an infarcted myocardium, orthotopic transplantation experiments with human CSs were performed. To do this, thawed (cryo-preserved) adult human CSs, coming from three atrial (one male and two female) and one ventricular (one female) biopsies were injected into the viable myocardium bordering a freshly produced infarct. Each mouse received CSs from a single passage of an explant (derived from a single subject). Four control infarcted animals were injected with an equal volume of PBS. After eighteen days from the intervention, the animals were sacrificed and infarct size was determined. Infarct size was $34.9 \pm 7.1$ (3.6) and $31.9 \pm 6.9$ (3.5) in the CS-treated group and PBS-injected group, respectively (p=n.s.). However, echocardiography showed better preservation of the infarcted anterior wall thickness ($0.80 \pm 0.29$ (0.15) versus $0.60 \pm 0.20$ (0.08) p=n.s.) and particularly of FS % ($36.85 \pm 16.43$ (8.21) versus $17.87 \pm 5.95$ (2.43) $p<0.05$) in the CS-treated group compared to the PBS-injected group (FIG. 3-table 1).

At the time of evaluation, bands of regenerating myocardium were present (with different degrees of organization and thickness) throughout most of the infarcted areas, as evaluated with hematoxylin-eosin histochemistry and MHC immunofluorescence (FIG. 3c). In the regenerating myocardium, cells expressing lamin A/C (a specific human nuclear marker) co-localize also with cardiomyocytes stained positive for MHC, newly generated capillaries stained for smooth α-actin and PECAM (FIG. 3c), and with connexin-43 expressing cells (which, as in the co-culture experiments, defines a connection between the human cells and the regenerating myocardium).

Thus CSs can be considered as clones of adult stem cells, maintaining their functional properties in vitro and in vivo also after cryo-preservation.

While this manuscript was in preparation, two papers have been published concerning the isolation of cardiac stem or progenitor cells from adult mammalian heart (28, 29). Isolation of these cells was based exclusively on the expression of a stem cell-related surface antigen: c-kit in the first paper and Sca-1 in the second one. In the first study (28) freshly isolated c-kit$^{pos}$ Lin$^-$ cells from rat heart were found to be self-renewing, clonogenic and multipotent, exhibiting biochemical differentiation into the myogenic, smooth muscle cell, or endothelial cell lineage but, differently from cells grown under the conditions described here, failed to contract spontaneously. When injected into an ischemic heart these cells regenerated functional myocardium. In the second study (29), Sca-1$^+$ ckit$^{neg}$ cells from mice heart were induced in vitro to differentiate toward the cardiac myogenic lineage in response to 5'-azacytidine. When given intravenously after ischemia/reperfusion, these cells homed to injured myocardium and differentiated into cardiomyocytes with and without fusion to host cells. Our data obtained on GFP-cKit transgenic mice also suggest that the adult cardiac stem cell is cKit$^{pos}$. It is possible that CSs enclose a mixed population of cells that, as a niche, could promote the viability of cKit progenitors and contribute to their proliferation. The data obtained in the present paper confirm the existence of an adult cardiac stem cell. More importantly, they demonstrate for the first time that it is possible to isolate cells from very small fragments of human myocardium and expand these cells in vitro many fold (reaching numbers that would be appropriate for in vivo transplantation in patients) without loosing their differentiation potential, thus opening previously unforeseen opportunities for myocardial repair.

Transgenic Mice

To follow the differentiation process of CSs during the pre- and post-natal age, MLC3F-nlacZ and TnI-nLacZ mice were utilized. These mice express a form of the lacZ transgene that localizes within the nucleus under the skeletal and cardiac muscle myosin light chain or cardiac troponin-I promoter, respectively (8, 9). CSs derived from embryonic day 9-12, fetal day 17-18, neonatal and adult mice, showed spontaneous expression of the reporter gene in a variable percentage (10-

Figure 4:
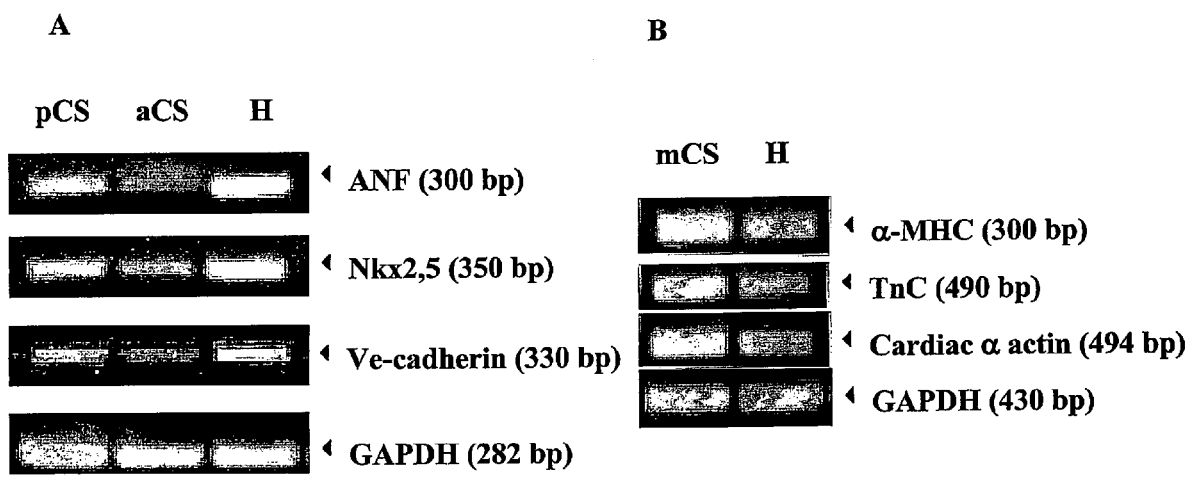
FIG. 4—a) (left) RT-PCR analysis of human CS from pediatric (pCS), adult (aCS) subjects and cardiac fragments (H) (ANF, NKx2.5, Ve-cadherin, GAPDH), and b) (right) RT-PCR analysis of murine CS (mCS) and of mouse heart fragments (H) (α-MHC, TnC, cardiac α-actin, GAPDH).

60%) of spheres at the different culture conditions employed (FIG. 4a). Moreover, the mouse CS start to beat at the start of formation (particularly in the embryo) and continue to beat over the course of their life span. The human CS expressed stem (CD-34, sca-1, cKit) and endothelial cell markers (flk-1, CD-31).

In order to further clarify the cellular origin of these spheres and to follow the pattern of their growth process, we utilized transgenic mice expressing the green fluorescent protein (GFP) under the control of the c-kit promoter (10). GFP-positive cells were present from the beginning of the formation of the CSs and, albeit with reduced fluorescence intensity, also later. Moreover, as suggested by the growth pattern of human CSs, when satellite secondary CSs appeared to detach from the primary ones, GFP-positive cells localized on the margins of the latter and in the inner part of the former. We studied this process in double-heterozygous mice obtained from EGFP-cKit/MLC3F-nlacZ or TnI-nLacZ crossings. As shown in FIG. 4b, beta-Gal-positivity did not co-localize with EGFP in cells present within the growing areas.

Genetic Phenotype

The RT-PCR panel created on murine or human CS RNA extracts is shown in FIG. 5. A more typical profile of cardiac progenitors seems to be that of the human samples (in log-growth phase) compared with the murine samples, in which it is easier to have proliferation and differentiation occurring together.

REFERENCES

1. Soonpaa M H, Field L J. Survey of studies examining mammalian cardiomyocyte DNA synthesis. Circ Res. 1998 Jul. 13; 83(1):15-26.
2. Nadal-Ginard B, Kajstura J, Leri A, Anversa P. Myocyte death, growth, and regeneration in cardiac hypertrophy and failure. Circ Res. 2003 Feb. 7; 92(2):139-50.
3. Laflamme M A, Myerson D, Saffitz J E, Murry C E. Evidence for cardiomyocyte repopulation by extracardiac progenitors in transplanted human hearts. Circ Res. 2002 Apr. 5; 90(6):634-40.
4. Glaser R, Lu M M, Narula N, Epstein J A. Smooth muscle cells, but not myocytes, of host origin in transplanted human hearts. Circulation. 2002 Jul. 2; 106(1):17-9.
5. Reffelmann T, Kloner R A. Cellular cardiomyoplasty—cardiomyocytes, skeletal myoblasts, or stem cells for regenerating myocardium and treatment of heart failure? Cardiovasc Res. 2003 May 1; 58(2):358-68.
6. Dowell J D, Rubart M, Pasumarthi K B, Soonpaa M H, Field U J. Myocyte and myogenic stem cell transplantation in the heart. Cardiovasc Res. 2003 May 1; 58(2):336-50.
7. Passier R, Mummery C. Origin and use of embryonic and adult stem cells in differentiation and tissue repair. Cardiovasc Res. 2003 May 1; 58(2):324-35.
8. Kelly R, Alonso S, Tajbakhsh S, Cossu G, Buckingham M. Myosin light chain 3F regulatory sequences confer regionalized cardiac and skeletal muscle expression in transgenic mice. J Cell Biol. 1995 April; 129(2):383-96.
9. Di Lisi R, Millino C, Calabria E, Altruda F, Schiaffino S, Ausoni S. Combinatorial cis-acting elements control tissue-specific activation of the cardiac troponin I gene in vitro and in vivo. J Biol. Chem. 1998 Sep. 25; 273(39):25371-80.
10. Cairns L A, Moroni E, Levantini E, Giorgetti A, Klinger F G, Ronzoni S, Tatangelo L, Tiveron C, De Felici M, Dolci S, Magli M C, Giglioni B, Ottolenghi S. c-kit regulatory elements required for expression in developing hematopoietic and germ cell lineages. Blood. 2003 Dec. 1; 102(12):3954-62.
11. Hadjantonakis A K, Gertsenstein M, Ikawa M, Okabe M, Nagy A. Generating green fluorescent mice by germline transmission of green fluorescent ES cells. Mech Dev. 1998 August; 76(1-2):79-90.
12. Follenzi A, Ailles L E, Bakovic S, Geuna M, Naldini L. Gene transfer by lentiviral vectors is limited by nuclear translocation and rescued by HIV-1 pol sequences. Nat Genet. 2000 June; 25(2):217-22.
13. Brooks W W, Garibaldi B A, Conrad C H. Myocardial injury in the mouse induced by transthoracic cauterization. Lab Anim Sci. 1998 August; 48(4):374-8.
14. Tajbakhsh S, Vivarelli E, Cusella-De Angelis G, Rocancourt D, Buckingham M, Cossu G. A population of myogenic cells derived from the mouse neural tube. Neuron. 1994 October; 13(4):813-21.
15. Ausoni S, Campione M, Picard A, Moretti P, Vitadello M, De Nardi C, Schiaffino S. Structure and regulation of the mouse cardiac troponin I gene. J Biol. Chem. 1994 Jan. 7; 269(1):339-46.
16. Ferrari S, Molinari S, Melchionna R, Cusella-De Angelis M G, Battini R, De Angelis L, Kelly R, Cossu G. Absence of MEF2 binding to the A/T-rich element in the muscle creatine kinase (MCK) enhancer correlates with lack of early expression of the MCK gene in embryonic mammalian muscle. Cell Growth Differ. 1997 January; 8(1):23-34.
17. Pennica D, King K L, Shaw K J, et al. Expression cloning of cardiotrophin1, a cytokine that induces cardiac myocyte hypertrophy. *Proc Natl Acad. Sci USA.* 1995; 92:1142-1146.
18. Sabri A, Guo J, Elouardighi H, Darrow A L, Andrade-Gordon P, Steinberg S F. Mechanisms of protease-activated receptor-4 actions in cardiomyocytes. Role of Src tyrosine kinase. J Biol. Chem. 2003 Mar. 28; 278(13):11714-20.
19. Zammit P S, Beauchamp jr. The skeletal muscle satellite cell: stem cell or son of stem cell? Differentiation 2001; 68:193-204.
20. Galli R, Gritti A, Bonfanti L, Vescovi Al. Neural Stem Cells: An Overview. Circ Res. 2003; 92: 598-608.
21. Layer Pg, Robitzki A, Rothermel A, Willbold E. Of Layers And Spheres: The Reaggregate Approach In Tissue Engineering. Trends Neurosci. 2002; 25:131-134.
22. Bates Rc, Edwards Ns, Yates Jd. Spheroids And Cell Survival. Crit Rev Oncol Hematol. 2000; 36:61-74.
23. Korff T, Augustin Hg. Integration Of Endothelial Cells In Multicellular Spheroids Prevents Apoptosis And Induces differentiation. J cell biol. 1998; 143:1341-1352.
24. Armstrong Mt, Lee Dy, Armstrong Pb. Regulation Of Proliferation Of The Fetal Myocardium. Dev Dyn. 2000; 219:226-36.
25. Svendsen Cn, Ter Borg Mg, Armstrong Rj, Rosser Ae, Chandran S, Ostenfeld T. Caldwell Ma. A New Method For The Rapid And Long Term Growth Of Human Neural Precursor Cells. J Neurosci Methods. 1998; 85:141-152.
26. Schofield R. The Relationship Between The Spleen Colony-Forming Cell And The Haemopoietic Stem Cell. Blood Cells. 1978; 4:7-25.
27. Kruithof Bp, Van Den Hoff Mj, Tesink-Taekema S, Moorman Af. Recruitment Of Intra- And Extracardiac Cells Into The Myocardial Lineage During Mouse Development. Anat Rec. 2003; 271a: 303-314.
28. Beltrami Ap, Barlucchi L, Torella D, Baker M, Limana F, Chimenti S, Kasahara H. Rota M, Musso E, Urbanek K, Leri A, Kajstura J, Nadal-Ginard B, Anversa P. Adult Car-

The invention claimed is:

1. A method to obtain stem cells able to repair damaged myocardiac tissue, comprising the following steps:
    fragmenting a cardiac tissue in vitro to obtain a plurality of tissue fragments;
    adhering said tissue fragments to a solid support;
    culturing said tissue fragments in a culture medium, wherein said culture medium comprises one or more nutrients and wherein said tissue fragments are sized to allow the diffusion of said nutrients to said tissue fragments;
    culturing said tissue fragments until one or more phase-bright cells form;
    harvesting the phase-bright cells;
    culturing the phase-bright cells on a treated substrate to generate one or more cardiospheres;
    wherein the cardiospheres form substantially spheroid structures of about 20 µm to about 150 µm in culture;
    wherein the cardiospheres are multicellular aggregates;
    wherein the cardiospheres comprise a mixed population of cells;
    wherein the mixed population comprises stem cells, cardiac cells, and endothelial cells,
    wherein the stem cells express at least one of the following three markers: CD34, c-kit and sca-1 within 12 hours of said cardiospheres being generated,
    wherein the endothelial cells express at least one of KDR, flk-1, and CD31 within 12 hours of said cardiospheres being generated,
    wherein the cardiospheres are weakly adherent or non-adherent to the treated substrate; and
    harvesting the cardiospheres, thereby obtaining stem cells for use in repairing damaged myocardiac tissue.

2. The method according to claim 1 wherein said cardiac tissue is derived from non-embryonic cardiac tissue biopsies.

3. The method according to claim 1 further comprising exposing at least one of said phase-bright cells or multicellular aggregates with oxygen concentrations different from that normally present in the atmosphere in order to modify the biologic characteristics of the phase-bright cells or multicellular aggregates.

4. The method according to claim 1 wherein said cardiospheres are able to generate continuous cell lines following spontaneous transformation or transformation induced by one or more chemical, physical or biologic agents.

5. The method according to claim 1 wherein the cardiospheres are fused with one or more other cells.

6. The method according to claim 1 wherein the cardiospheres are used for nuclear transfer to and from one or more other cells.

7. The method according to claim 1 wherein the cardiospheres are grown in at least one stage on a biodegradable and/or biocompatible supports.

8. The method according to claim 1 wherein the cardiospheres are cultured in at least one of a bioreactor or fermenter.

9. The method according to claim 1, further comprising disassociating the multicellular aggregates into a plurality of single cells.

10. The method according to claim 1, wherein the cardiospheres are generally spheroid in shape.

11. The method according to claim 1, wherein the cardiospheres form substantially spheroid structures of about 20 μm to about 150 μm in size after about 48 hours to about 72 hours of culture.

12. The method according to claim 1, wherein the mixed cell population further comprises vascular cells, and wherein the vascular cells express smooth alpha actin.

13. The method according to claim 1, wherein the treated substrate comprises a polylysine-treated cellular substrate that is horse-serum-free.

14. The method according to claim 1, wherein the cardiospheres are clonal-derived.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: hNkx forw primer

<400> SEQUENCE: 1
ctcccaacat gaccctgagt                                                    20

<210> SEQ ID NO 2
<211> LENGTH: 20
<212> TYPE: DNA
<213> ORGANISM: Artificial
<220> FEATURE:
<223> OTHER INFORMATION: hNkx rev primer

<400> SEQUENCE: 2
gagctcagtc ccagttccaa                                                    20

<210> SEQ ID NO 3
<211> LENGTH: 20
<212> TYPE: DNA
<213> ORGANISM: Artificial
<220> FEATURE:
<223> OTHER INFORMATION: hANF forw primer

<400> SEQUENCE: 3
aatcaagttc agaggatggg                                                    20

<210> SEQ ID NO 4
<211> LENGTH: 20
<212> TYPE: DNA
<213> ORGANISM: Artificial
<220> FEATURE:
<223> OTHER INFORMATION: hANF rev primer

<400> SEQUENCE: 4
aatgcatggg gtgggagagg                                                    20

<210> SEQ ID NO 5
<211> LENGTH: 18
<212> TYPE: DNA
<213> ORGANISM: Artificial
<220> FEATURE:
<223> OTHER INFORMATION: hVe-Cad forw primer

<400> SEQUENCE: 5
tctctgtcct ctgcacaa                                                      18

<210> SEQ ID NO 6
<211> LENGTH: 18
<212> TYPE: DNA
<213> ORGANISM: Artificial
<220> FEATURE:
<223> OTHER INFORMATION: hVe-Cad rev primer

<400> SEQUENCE: 6

```
atgcagaggc tcatgatg                                                 18
```

<210> SEQ ID NO 7
<211> LENGTH: 20
<212> TYPE: DNA
<213> ORGANISM: Artificial
<220> FEATURE:
<223> OTHER INFORMATION: hGAPDH forw primer

<400> SEQUENCE: 7

```
gaagagccaa ggacaggtac                                               20
```

<210> SEQ ID NO 8
<211> LENGTH: 20
<212> TYPE: DNA
<213> ORGANISM: Artificial
<220> FEATURE:
<223> OTHER INFORMATION: hGAPDH rev primer

<400> SEQUENCE: 8

```
ctgcaccacc aactgcttag                                               20
```

<210> SEQ ID NO 9
<211> LENGTH: 24
<212> TYPE: DNA
<213> ORGANISM: Artificial
<220> FEATURE:
<223> OTHER INFORMATION: mMHC forw primer

<400> SEQUENCE: 9

```
gaagagtgag cggcgcatca agga                                          24
```

<210> SEQ ID NO 10
<211> LENGTH: 23
<212> TYPE: DNA
<213> ORGANISM: Artificial
<220> FEATURE:
<223> OTHER INFORMATION: mMHC rev primer

<400> SEQUENCE: 10

```
tctgctggag aggttattcc tcg                                           23
```

<210> SEQ ID NO 11
<211> LENGTH: 24
<212> TYPE: DNA
<213> ORGANISM: Artificial
<220> FEATURE:
<223> OTHER INFORMATION: m cardiac actin forw primer

<400> SEQUENCE: 11

```
tgttacgtcg ccttggattt tgag                                          24
```

<210> SEQ ID NO 12
<211> LENGTH: 22
<212> TYPE: DNA
<213> ORGANISM: Artificial
<220> FEATURE:
<223> OTHER INFORMATION: m cardiac actin rev primer

<400> SEQUENCE: 12

```
aagagagaga catatcagaa gc                                            22
```

<210> SEQ ID NO 13
<211> LENGTH: 20
<212> TYPE: DNA
<213> ORGANISM: Artificial
<220> FEATURE:

```
<223> OTHER INFORMATION: m cardiac TnC forw primer

<400> SEQUENCE: 13
aatggatgac atctacaaag                                              20

<210> SEQ ID NO 14
<211> LENGTH: 20
<212> TYPE: DNA
<213> ORGANISM: Artificial
<220> FEATURE:
<223> OTHER INFORMATION: m cardiac TnC rev primer

<400> SEQUENCE: 14
tgagctcttc aatgtcatct                                              20

<210> SEQ ID NO 15
<211> LENGTH: 20
<212> TYPE: DNA
<213> ORGANISM: Artificial
<220> FEATURE:
<223> OTHER INFORMATION: mGAPDH forw primer

<400> SEQUENCE: 15
cctctggaaa gctgtggcgt                                              20

<210> SEQ ID NO 16
<211> LENGTH: 20
<212> TYPE: DNA
<213> ORGANISM: Artificial
<220> FEATURE:
<223> OTHER INFORMATION: mGAPDH rev primer

<400> SEQUENCE: 16
ttggaggcca tgtaggccat                                              20
```